United States Patent [19]

Bailey et al.

[11] 4,347,378

[45] Aug. 31, 1982

[54] ANTIMICROBIAL GLYCOLIC ACID DERIVATIVES

[75] Inventors: August V. Bailey, New Orleans; Gordon J. Boudreaux, Metairie; Gene Sumrell, New Orleans, all of La.

[73] Assignee: The United States of America as represented by the Secretary of Agriculture, Washington, D.C.

[21] Appl. No.: 308,350

[22] Filed: Oct. 5, 1981

Related U.S. Application Data

[62] Division of Ser. No. 235,812, Feb. 19, 1981.

[51] Int. Cl.$^3$ .............................................. C07C 69/76
[52] U.S. Cl. .................................. 560/105; 560/196; 560/222; 260/404
[58] Field of Search ........................................ 560/105

[56] References Cited

FOREIGN PATENT DOCUMENTS 44-27020 11/1969 Japan ................................... 560/105

*Primary Examiner*—Paul J. Killos
*Attorney, Agent, or Firm*—M. Howard Silverstein; David G. McConnell; Raymond C. Von Bodungen

[57] ABSTRACT

Esters and mixed ester-amides derived from glycolic acid by substitution at the hydroxyl and carboxyl functions were prepared by conventional procedures and tested for antimicrobial activity. All of the compounds tested showed some inhibition against four microorganisms under the test conditions, and some of them had potent activity. These new compounds have properties which make it possible for them to be used as biostatic agents in commercial products.

2 Claims, No Drawings

ANTIMICROBIAL GLYCOLIC ACID DERIVATIVES

This is a division of application Ser. No. 235,812, filed Feb. 19, 1981.

BACKGROUND OF THE INVENTION (1) Field of the Invention

This invention relates to certain ester and ester-amide derivatives of glycolic acid which have exhibited antimicrobial activity.

(2) Description of the Prior Art

The germicidal activity of certain lipid compounds has long been known. Soap is a familiar example. Various fatty acids and their derivatives have found use as antiseptics and disinfectants, and also as preservatives for drugs and cosmetics. In recent times, however, the fatty antimicrobials have to a considerable degree been replaced for such applications by more potent synthetic non-fatty compounds. More recently, many of the latter materials have come under suspicion by regulatory agencies because of their toxicity and side reactions. The pendulum is swinging back in favor of naturally occurring or derived lipid materials for application as antimicrobials and preservatives in food, pharmaceuticals, and other organic materials of commerce which are subject to bacterial or fungal attack, and in the formulation of self-preserving cosmetics.

In the search for antimicrobial agents for use in commercial products, it is necessary to ascertain the relative degree of inhibition that can be attained with any specific microorganisms under normal conditions of product use in accordance with the chemical and physical properties of the product. Minor differences in structure may result in one compound being inactive while a very similar compound has potent broad spectrum antimicrobial activity. Also, some compounds may be selectively active against only one or a small number of microorganisms, while another very similar compound shows a broad spectrum of activity against many types of organisms. Thus, screening is necessary in evaluating new compounds for potential use as antimicrobial agents, followed by intensive testing for specific end uses of those compounds found to have antimicrobial activity.

SUMMARY OF THE INVENTION

This invention involves the use of conventional procedures to prepare some new compounds based on substitution of glycolic acid at both the hydroxy and carboxylic acid groupings to yield esters and ester-amides, and the discovery that some of these materials are antimicrobially active. These new compounds have the following structures:

(RCOOCH₂CH₂)₂NCOCH₂OOCR  (1)

C₆H₅CH₂CH₂COOCH₂COOR'  (2)

R'OOCCH₂OOCCH₂CH₂CH₂CH₂COOCH₂COOR'  (3)

where R is an alkyl or alkenyl group of 4 to 17 carbon atoms, and R' is an alkyl group of 1 to 4 carbons. R and R' may be straight-chained or branched.

The new fatty amides and esters that are the subject of this invention are characterized by the fact that as growth inhibitors they are effective against a variety of microorganisms that include bacteria, yeasts, and molds. Some of these compounds exhibit broad antimicrobial spectrum, whereas others exhibit selective antimicrobial spectrum. The relatively low toxicity of fatty-derived compounds to humans in comparison to most antimicrobially active materials currently used as additives in food and other commercial products has caused renewed interest in fatty derivatives as biostatic additives.

DESCRIPTION OF THE PREFERRED EMBODIMENTS

The compounds which are the subject of this invention are certain glycolic acid derivatives which are substituted at the hydroxy and carboxyl functions and have the following structures:

(RCOOCH₂CH₂)₂NCOCH₂OOCR  (1)

C₆H₅CH₂CH₂COOCH₂COOR'  (2)

R'OOCCH₂OOCCH₂CH₂CH₂CH₂COOCH₂COOR'  (3)

where R is an alkyl or alkenyl group of 4 to 17 carbon atoms and R' is a lower alkyl group of 1 to 4 carbons. R and R' may be straight-chained or branched. These compounds were prepared by conventional procedures.

The bioactivity of these compounds has been established by applicants in vitro but, as will be apparent to those skilled in the arts pertaining to the growth inhibition of bacteria, yeasts, and molds, the compounds, besides being used as such, will for utilitarian purposes commonly be formulated using a diluent that can be either liquid, viscous, or solid.

A wide variety of extending agents is operable, the only significant requirement being that the diluent or extender be inert with respect to the compound involved. Petroleum jellies, various alcohols and polyols, vegetable oils and the like are suitable.

Difco Bacto dehydrated nutrient agar at pH 6.8, Difco Bacto dehydrated yeast mycological agar at pH 4.5, and Difco dehydrated mycological agar at pH 7.0 were used to test inhibition of the bacteria, yeast, and mold cultures, respectively. The microorganisms used were obtained from stock cultures. After the cultures were incubated for 48 hours at room temperature, suspensions of the microorganisms were prepared. One loop (⅛ inch) of spores of sporeformers was removed from the cultures and placed in 5 ml sterile 0.5% saline solution. With nonspore formers, one loop of vegetative cells was suspended in 5 ml sterile 0.5% saline solution. The suspension served as the inoculum for the estimation of activity against microbial growth.

Hardened agar plates were inoculated by placing 3 drops of the suspension on the agar. Microorganisms were spread over the surface of the plates with sterile glass rods. These plates were employed in the activity estimation against microbial growth. Paper discs 6.5 mm in diameter, made from Whatman No. 1 filter paper, were used in the evaluation of the liquid compounds, and stainless steel cylinders of 5 mm inside diameter were used for the solid compounds. The paper discs, completely saturated with the liquid test compound, were placed on the surface of agar plates inoculated with test organisms. Solid compounds were placed in stainless steel cylinders in direct contact with the inoculated plates. No carrier solvent was employed. To eliminate any errors which could result from an insufficient number of tests, a minimum of three experiments, at different times, employing duplicate plates were made for each compound under test. All plates were incubated at the optimum growing temperature for each organism and readings were taken after 24, 48, 72, and 120 hour periods.

The organisms used in the tests were: a gram-positive bacterium, *Staphylococcus aureus;* a gram-negative bacterium, *Escherichia coli;* a yeast, *Candida utilis;* and a mold, *Penicillium species.* The data from these tests are tabulated in Table I.

Specific examples showing the preparation of each of the new compounds being claimed are set forth below along with appropriate data in tabular form which is being submitted for the purpose of establishing the growth inhibiting properties of the claimed compounds.

EXAMPLE 1

N,N-bis(Pelargonoyloxyethyl)pelargonoylacetamide 106 g (0.6 mole) of pelargonoyl chloride was added dropwise with stirring to a solution of 32.6 g (0.2 mole) of N,N-bis(hydroxyethyl)hydroxyacetamide in 60 ml of pyridine. The precipitated pyridine hydrochloride was filtered, washed with benzene, and discarded. The benzene solution of product was water washed, dried over sodium sulfate, and passed through an activated alumina column to remove any acid. The benzene was stripped off an a rotary evaporator. The yield of product was essentially quantitative. Its structure was established by infrared and nuclear magnetic resonance spectroscopy. It had $n_D^{30}$ 1.4537 and $d_4^{30}$ 0.9745.

EXAMPLE 2

N,N-bis(Lauroyloxyethyl)lauroyloxyacetamide

This compound was prepared from 131 g (0.6 mole) of lauroyl chloride and 32.6 g (0.2 mole) of N,N-bis(hydroxyethyl)hydroxyacetamide by the procedure of Example 1. Its structure was established by infrared and nuclear magnetic resonance spectroscopy. It was a low-melting solid and had $n_D^{30}$ 1.4597 and m.p. 29.6° C.

EXAMPLE 3

N,N-bis(Oleoyloxyethyl)oleoyloxyacetamide

This compound was prepared from 181 g (0.6 mole) of oleoyl chloride and 32.6 g (0.2 mole) of N,N-bis(hydroxyethyl)hydroxyacetamide by the procedure of Example 1. Its structure was established by infrared and nuclear magnetic resonance spectroscopy. It had $n_D^{30}$ 1.4731 and $d_4^{30}$ 0.9383.

EXAMPLE 4

N,N-bis(Trimethylacetyloxyethyl)trimethylacetyloxyacetamide

This compound was prepared from 73 g (0.6 mole) of trimethylacetyl chloride and 32.6 g (0.2 mole) of N,N-bis(hydroxyethyl)hydroxyacetamide by the procedure of Example 1. Its structure was established by infrared and nuclear magnetic resonance spectroscopy. It was a white solid with m.p. 51.4° C.

EXAMPLE 5

Carboethoxymethyl hydrocinnamate 33.7 g (0.2 mole) of hydrocinnamoyl chloride was added to a stirred solution of 18 g (0.2 mole) of ethyl glycolate in 20 ml of pyridine. The precipitated pyridine hydrochloride was filtered, washed with benzene, and discarded. The benzene solution of carboethoxymethyl hydrocinnamate was water washed, dried over sodium sulfate, and the solvent stripped off using a rotary evaporator. The yield of product was essentially quantitative. Its structure was established by infrared and nuclear magnetic resonance spectroscopy. It had $n_D^{30}$ 1.4900 and $d_4^{30}$ 1.0919.

EXAMPLE 6 bis(Carbomethoxymethyl) adipate

This compound was prepared from 36 g (0.4 mole) of methyl glycolate and 36.6 g (0.2 mole) of adipoyl chloride by the procedure of Example 5. Its structure was established by infrared and nuclear magnetic resonance spectroscopy. It had $n_D^{30}$ 1.4445 and $d_4^{30}$ 1.1961.

TABLE I

| | ANTIMICROBIAL ACTIVITY OF GLYCOLIC ACID DERIVATIVES | | | | |
|---|---|---|---|---|---|
| | | Antimicrobial activity[a] microorganisms[b] | | | |
| No. | Compound | A | B | C | D |
| 1 | N,N-bis(Pelargonoyloxyethyl)pelargonoyloxyacetamide | ∞ | ∞ | + | ∞ |
| 2 | N,N-bis(Lauroyloxyethyl)lauroyloxyacetamide | o | o | ∞ | ∞ |
| 3 | N,N-bis(Oleoyloxyethyl)oleoyloxyacetamide | o | o | o | o |
| 4 | N,N-bis(Trimethylacetyloxyethyl)trimethylacetyloxyacetamide | + | o | ++ | + |
| 5 | Carboethoxymethyl hydrocinnamate | ∞ | ∞ | + | ∞ |
| 6 | bis(Carbomethoxymethyl) adipate | + | + | ++ | ++ |

[a] ++ = Zone of inhibition at least 0.5 cm beyond disc or cylinder area at 120 hr.
+ = Zone of inhibition less than 0.5 cm beyond disc or cylinder area at 120 hr.
∞ = Organism failed to grow on disc or cylinder area at 120 hr.
o = Slight growth on the disc or cylinder area at 120 hr.
[b] A = *Staphylococcus aureus.*
B = *Escherichia coli.*
C = *Candida utilis.*
D = *Penicillium species.*

We claim:
1. A diester of glycolic acid having antimicrobial activity and the general structure:

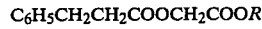

$C_6H_5CH_2CH_2COOCH_2COOR$ where R is an alkyl group of 1 to 4 carbon atoms and may be branched or unbranched.

2. The diester of claim 1 wherein the compound is carboethoxymethyl hydrocinnamate.

* * * * *